United States Patent [19]

Lagier

[11] Patent Number: 4,712,201

[45] Date of Patent: Dec. 8, 1987

[54] ACOUSTIC SELF-GUIDANCE SYSTEMS FOR SUBMARINE VEHICLES

[75] Inventor: Michel Lagier, Paris, France

[73] Assignee: Thomson CSF, Paris, France

[21] Appl. No.: 22,115

[22] Filed: Feb. 16, 1979

[30] Foreign Application Priority Data

Feb. 17, 1978 [FR] France ................. 78 04526

[51] Int. Cl.$^4$ .............................. G01S 9/66
[52] U.S. Cl. ............................ 367/92; 367/96
[58] Field of Search .............. 367/92, 96; 114/23

[56] References Cited

U.S. PATENT DOCUMENTS

3,723,954  3/1973  Nelkin et al. ................. 367/96
3,864,666  2/1975  Douglas ....................... 367/96
3,924,259 12/1975  Butler et al. ................. 367/92

Primary Examiner—Stephen C. Buczinski
Assistant Examiner—Melissa L. Koltak
Attorney, Agent, or Firm—Cushman, Darby & Cushman

[57] ABSTRACT

A self-guidance system for submarine vehicles containing a parametric sonar including preformed channel, transmission device and, in each channel, two beams at the primary frequencies formed simultaneously. Reception takes place with preformed beams at the primary and the secondary frequencies followed by a filter giving frequential channels. An echo comparator receives the signals at the primary and secondary frequencies and enables interference echoes from decoys in particular to be eliminated and the rudders to be controlled.

11 Claims, 12 Drawing Figures

Fig_1

Fig_2

Fig_3

Fig_4

Fig_5

Fig_8

Fig_9

ACOUSTIC SELF-GUIDANCE SYSTEMS FOR SUBMARINE VEHICLES

BACKGROUND OF THE INVENTION

The present invention covers the improvement of acoustic self-guidance systems for submarine vehicles.

The invention is applicable more especially to the guidance of torpedoes towards a target, which contain an active sonar, when a torpedo is moving in shallow water or near a reverberating surface. It makes it possible also to distinguish between true and false targets such as decoys.

In such a system, a target detection level is sought which is high enough with respect to reverberation from the surface and sea bottom, the reverberation level being proportional to the angular aperture of the acoustic beam in the horizontal plane (bearing). The front dimensions of torpedoes and of the acoustic transducers fixed on the torpedo head are of the order of 250 mm. Hence, if it is necessary to operate with a bearing aperture of less than 3°, operation must be at frequencies higher than 100 kHz, which will be called high frequencies, for which absorption in the marine medium is high. This reduces the range.

To correct this disadvantage, it is known that the sonic energy can be passed in metallic bars of length L situated in the vehicle's sides along an axis parallel to that of the vehicle's motion under conditions such that the energy be concentrated in a direction at an angle of $\Psi$ with respect to this axis.

The apparent dimension of the transmitting transducer being $L \sin \Psi$, beam widths of the order of 10° at 10 kHz can be obtained. However, because of flow noises when the vehicle moves, the best position for the acoustic transducers is still the front surface of the vehicle.

A solution to reduce the reverberation noise can be found in U.S. Pat. No. 3,723,954, which consists in filtering the useful signal around the frequency shifted by the Doppler effect due to the torpedo to target relative speed.

The disadvantge is that attenuation of the reverberation depends on the target speed.

It is known that the directivity of a sonar receiving at low frequency (frequency less than 30 kHz) can be increased by producing a parametric effect of two directional beams transmitting simultaneously at high frequency. This effect is obtained thanks to the non-linear properties of sea-water. It is also known that multiple channels can be formed in a parametric sonar as is shown in the American report AD-AO 22 215 naval research distributed by the NTIS. Two high frequency beams correspond to each space channel on transmission, their difference in frequency varying from one channel to another which enables the low frequency overall reception channels to be filtered. The reception channels thus formed are called "frequential channels". This device has the disadvantage of requiring transmission on as many frequencies as there are channels plus one.

SUMMARY OF THE INVENTION

In accordance with the present invention, the principle of the non-linear interaction of two high frequency beams transmitted simultaneously with multiple channels is used, the angular aperture of each channel in bearing being a few degrees, to reduce the reverberation noise. On reception at low frequency, channels are formed and this reduces the number of different high frequencies required on transmission. They receive simultaneously at high and low frequencies and this makes identification of the targets easier.

More precisely, the invention covers a self-guidance system for a submarine vehicle using an active sonar with at least one transmission and reception transducers and means for preforming multiple spatial channels on transmission in an angular aperture sector in bearing. The invention is characterized by the fact that the sonar is parametric, that the angular sector is divided into r sectors, that in each sector q beams or spatial channels are preformed, that in each of these channels two beams are transmitted simultaneously at so-called primary or high frequencies F and $F_i$, $F_i$ varying from one channel to another in the same sector, that r spatial channels are preformed on reception corresponding to the r sectors and that the signals in each reception channel are filtered by q filters placed in parallel and centered on the secondary low frequencies $f_1 = F - F_1$, $f_2 = F - F_2$, ... $f_i = F - F_i$ ... $f_q = F - F_q$, the q signals filtered forming the reception channels called frequential channels.

BRIEF DESCRIPTION OF THE DRAWINGS

Other objects and many of the attendant advantages of this invention will be readily appreciated as the same become better understood, by reference to the following detailed description, when considered in connection with the accompanying drawings wherein.

DESCRIPTION OF THE INVENTION

Figure 1:
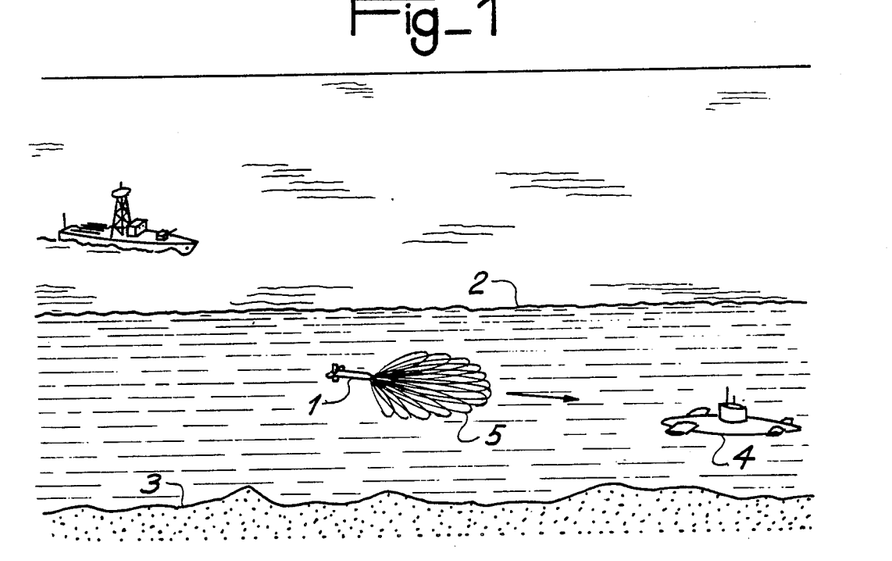
FIG. 1 shows a submarine vehicle and its target in the medium in which they move.

FIG. 1 shows a self-propelled submarine vehicle 1 of the torpedo type moving between the surface 2 and the bed 3 of the sea towards a target 4. The sonar radiation diagrams are shown with the channels 5 in bearing.

It is known that the coverage of the space by an acoustic guiding system requires that the vertical aperture, called the elevation aperture, be such that a fraction of the energy transmitted unfortunately reaches the sea surface and bed. This surface and bed return this fraction of energy in all directions but in a very variable fashion depending on the state of the surface and the type of bed.

Figure 2:
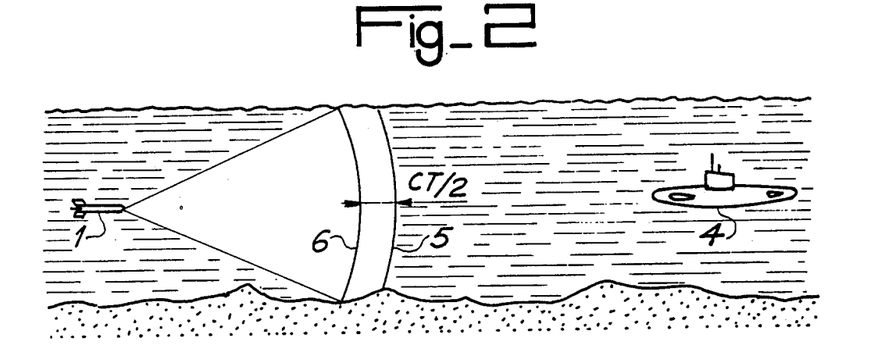
FIG. 2 shows a vertical section of the said medium.
Figure 3:
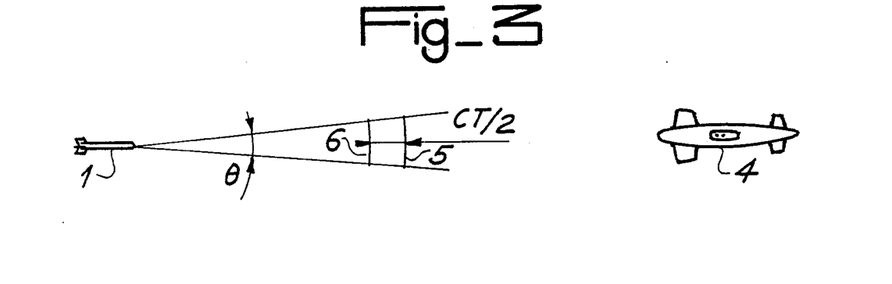
FIG. 3 shows a horizontal view of the said medium with the reverberation surface.

The problems caused by reverberation from the surface and bed are shown in FIGS. 2 and 3. The sonar transmits pulses of duration T and, because of the reverberation, the reception antenna, at a given instant, receives power proportional to $CT\theta/2$ in which C is the speed of propagation of sound in the medium and $\theta$ the bearing aperture.

FIG. 2 is a view in a vertical plane and shows the wave surfaces 5 and 6 of the beginning and end of the pulse which return at a given instant. FIG. 3 shows these wave surfaces in a horizontal plane.

The aperture $\theta$ in bearing of the radiation diagram at 3 dB of a sonar is given by the relation $\theta \simeq \lambda/d$ in which d is the length in the horizontal plane and $\lambda$ the wave length in the propagation medium. As d must be less than 250 mm, which is the maximum front dimension of a torpedo, for $\theta$ to be of the order of 3°, a frequency of the order of 100 kHz must be used. At such a frequency the absorption in the propagation medium is too high for the detection of targets more than 1000 m away. To deal with this problem, in the parametric sonar in accordance with the invention, two beams are formed on transmission. This takes place simultaneously in each channel i at two so-called primary frequencies, F and $F_i$ (high frequency) and reception takes place at the secondary frequency $f_i = F - F_i$ (low frequency). Reception channels are also formed at low frequency. When the submarine vehicle is sufficiently near the target (attack phase), reception also takes place at high frequency at $F_i$. In this last case, a comparison of the high and low frequency echoes makes it possible to distinguish between a target and a decoy.

In spite of the low output of the parametric frequency change, which gives a power loss of $G_1$ in dB, the gain $G_2$, which is also in dB, due to the fact that propagation takes place at a lower frequency, is such that $G_2 + G_1 > 0$.

Thus, for an acoustic power of 1 kW, a vehicle to target range of 700 m, primary frequencies around 120 kHz and a secondary frequency at 30 kHz, the comparison for the same bearing aperture with d = 250 mm between a linear and a parametric acoustic sonar gives:

$G_1 = -31$ dB and $G_2 = +84$ dB whence $G_1 + G_2 = 53$ dB.

This shows the great superiority of the parametric sonar for ranges of more than 700 m.

The directivity diagram of the secondary beam $D_s(\beta)$ in which $\beta$ is the angle with the mean direction is such that:

$$D_s(\beta) = (D_p(\beta))^2 \qquad (1)$$

in which $D_p(\beta)$ is the transmission diagram at the primary frequency.

The relation (1) corresponds to negligible directivity on reception and a sufficiently high absorption for the primary frequencies for the secondary transmission fictitious antenna, called "end fire", to be practically the same as the primary transmission transducer. As a result, the angular aperture at 3 dB, $\theta_s$, corresponding to $D_s(\beta)$ is such that $\theta_s = 0.64\lambda/d$ in which $\lambda$ is the mean primary wave length.

In accordance with the invention, the space suveyed in bearing corresponds to an angle $\theta_m$. This aperture is divided into r sectors each containing q preformed beams or spatial channels. In each of the channels, transmission occurs simultaneously at two frequencies, F and $F_i$. In one of the sectors all the frequencies $F_i$ are different from one sub-sector to the other. There is then a common frequency F with q other frequencies for the q channels of each sector.

On reception of the secondary signal low frequency signal, r beams or spatial channels are preformed and, at the output of each channel, q filters are placed, which are tuned to the secondary frequencies $f_i$. Low frequency frequential channels are thus formed. The filter band width allows for the Doppler effect due to the torpedo to target relative speed.

In a preferred embodiment, $\theta_m = 60°$, r = 3 and q = 10.

Figure 4:
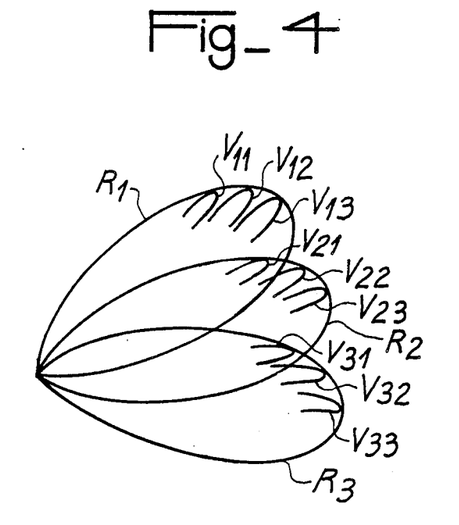
FIG. 4 shows the cover in bearing by the low frequency channels.

FIG. 4 shows the transmission diagrams for three spatial reception channels (r = 3), $R_1$, $R_2$ and $R_3$ and the channels $V_{11}$, $V_{12} \ldots V_{1q}$ of the sector corresponding to reception diagram $R_1$, the frequential channels $V_{21}$, $V_{22} \ldots V_{2q}$ corresponding to reception diagram $R_2$ and finally frequential channels $V_{31}$, $V_{32} \ldots V_{3q}$ corresponding to reception diagram $R_3$.

In this preferred embodiment, the space surveyed in bearing is 60° and the cover for this space is obtained with 30 channels in 30 different directions and three sectors. A simultaneously transmission on frequencies F and $F_i$ corresponds to each channel in which i varies from 1 to 10. F = 140 kHz is used and the $F_i$s are around 110 kHz. The bearing aperture is 15°.

In accordance with the invention, not only frequential reception channels are formed by filtering at the secondary frequencies $f_i$ but also frequential reception channels by filtering at the primary frequencies $F_i$ and the data received at the primary and secondary frequencies are processed simultaneously.

The data received at the high and low frequencies come, through each of the corresponding channels, from the same area in space but they are reflected with a very different variance because the wave lengths are very different. When the data received at the primary frequency $F_i$ are of a high enough level to be processed, the distance from the vehicle to the target is much less than what it was at the beginning of the search because the range of these frequencies is reduced by absorption. In other words, the submarine vehicle has "acquired" the target for some time and the field of action no longer needs to be so big. This is why in the close-up phase only one high frequency spatial reception channel is formed along the axis of the vehicle's advance. Direction selection is made, as for the reception channels at the secondary frequencies $f_i$, by N' filters tuned to the frequencies $F_i$, i varying from 1 to N'. The overall transmission plus reception directivity of these "high frequency" channels $D_{p_s}(\beta)$ is almost the same as that of the "low frequency" channels since $D_{p_s}(\beta) = D_{p_r}(\beta)^2$ from which $D_{p_s}(\beta) = D_r(\beta)$ from relation (1).

An example of the production of preformed channels on "high frequency" reception is:

spatial channel aperture: 20°
number of "frequency $F_i$" channels: N' = 10
"frequency $f_i$" channel aperture: 3°

Figure 5:
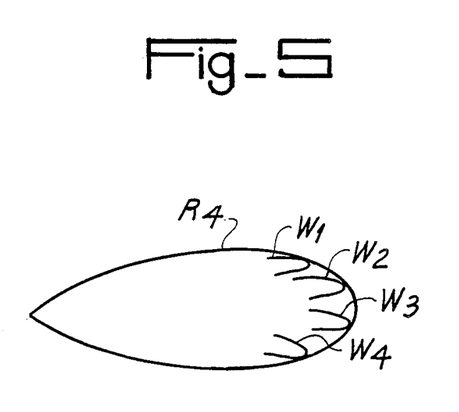
FIG. 5 shows the cover in bearing by the high frequency channels.

FIG. 5 shows the transmission diagrams of channels $W_1, W_2, \ldots$ corresponding to the primary frequencies $F_1, F_2, \ldots$ and the reception diagram $R_4$.

The fact of receiving echoes at the primary and secondary frequencies during the approach phase is a characteristic of the invention. This enables a target to be distinguished from a "decoy" of the responder type because "decoys" have much smaller dimensions than submarines and the responder characteristics depend on the frequency.

To determine the dimensions of the target, the fact is used that several echoes much exist simultaneously in several channels at close range when they come from a target.

Also, a simple comparison during several recurrences of the presence or absence of echoes in the two types of channel removes any doubt.

Hence, when only one echo is present in all the primary and secondary reception channels throughout several recurrences, this echo is not due to a target such as a submarine which, at close range, will produce echoes in several channels simultaneously. In accordance with the invention, in this case, a logic circuit supplies a signal to the torpedo rudder control circuit for it to resume the search for the target being tracked.

In accordance with the invention, an attempt has been made to reduce considerably the number and volume of the electronic components used to form the transmission and reception spatial channels. To do this, components of the "charge coupled device" type or (CCD) are used.

The properties of these components and their applications in the formation of spatial channels are given in the report by White and Webb entitled "A study of the use of charge coupled devices in signal analog processing systems" (Westinghouse Defense and Electronic Systems Center, Baltimore), dated May 1974 (NTIS publication AD-783 703). This technique of multiple analog sampling and delaying has the advantage over classical digital processing that it requires fewer elements. In particular, it makes possible the elimination of the digital-analog and analog-digital converters together with the n shift registers corresponding to the n bits of amplitude quantification.

Figure 6:
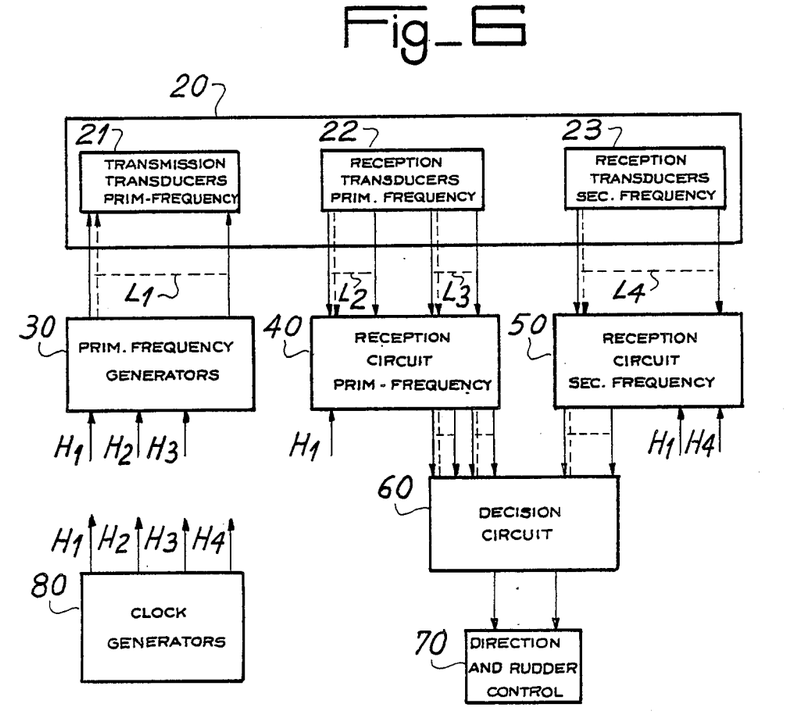
FIG. 6 shows general block diagram of the sonar for self-guidance.

FIG. 6 shows a general schematic diagram of the parametric sonar and the processing of the signals for control of the torpedo rudders in accordance with the invention.

The transmission-reception antenna 20 contains the assembly of transmission transducers 21, the assembly of reception transducers 22 at the primary frequencies and the assembly of reception transducers 23 at the secondary frequencies. 80 represents the circuits supplying the clock signals $H_1$, $H_2$, $H_3$ and $H_4$. The transmission transducers 21 receive the signals at the primary frequencies from the generator 30. The signals received by transducers 22 and 23 are processed by reception assemblies 40 and 50 respectively. 60 is a decision circuit using signals at the primary and secondary frequencies and 70 represents the torpedo direction and dive rudder controls.

In accordance with the invention, the data supplied by reception circuits 40 and 50 are used to obtain an estimation of the target bearing. In classical systems, the diagram aperture is such that only a small number of channels, two or three, are usually formed. As a result, division of the space only allows a small number of decisions to be made concerning the amplitude of the movement to be given to the rudder controls 70.

By dividing up the space in accordance with the invention into a large number of sectors, 30 for example, it is possible to give a weight to each of the channels in order to define, for each one of them, a direction instruction which is a function of its level. Piloting of the vehicle in elevation is done in classical fashion; the phase of the signals received by the transducers used to produce the reception channels at the primary frequencies and other transducers arranged for this purpose at a vertical distance of $\lambda/2$ is compared.

Figure 7:
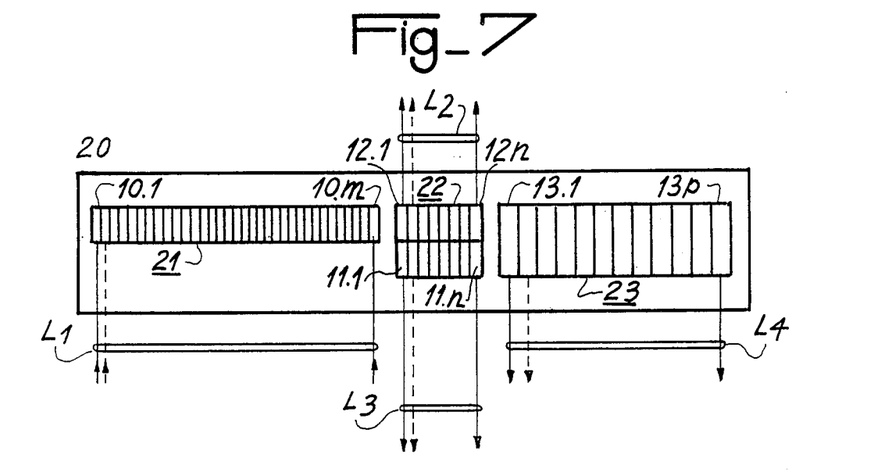
FIG. 7 shows the schematic diagram of the transducer network.

Transducer assembly 20 is shown in FIG. 7. Transducers 10.1, . . . 10.m are high frequency transducers working on transmission only. They are connected to generator 30 by the links $L_1$. Transducers 11.1, . . . 11.n are intended for the formation of the primary high frequency reception channels connected to reception assembly 40 by the links $L_2$. The group of transducers 12.1, . . . 12.n connected to reception assembly 40 by the links $L_3$ has exactly the same functions as the group of transducers 11.1 to 11.n. They are placed under the first ones respectively in such a way that a phase comparison channel by channel can be made in order to guide the vehicle in elevation during the final approach phase.

The p low frequency reception transducers 13.1, 13.2, 13.3, . . . 13.p are also shown connected to reception assembly 50 by the links $L_4$. For clearness in the drawing, these transducers do not fill the whole antenna width.

Figure 8:
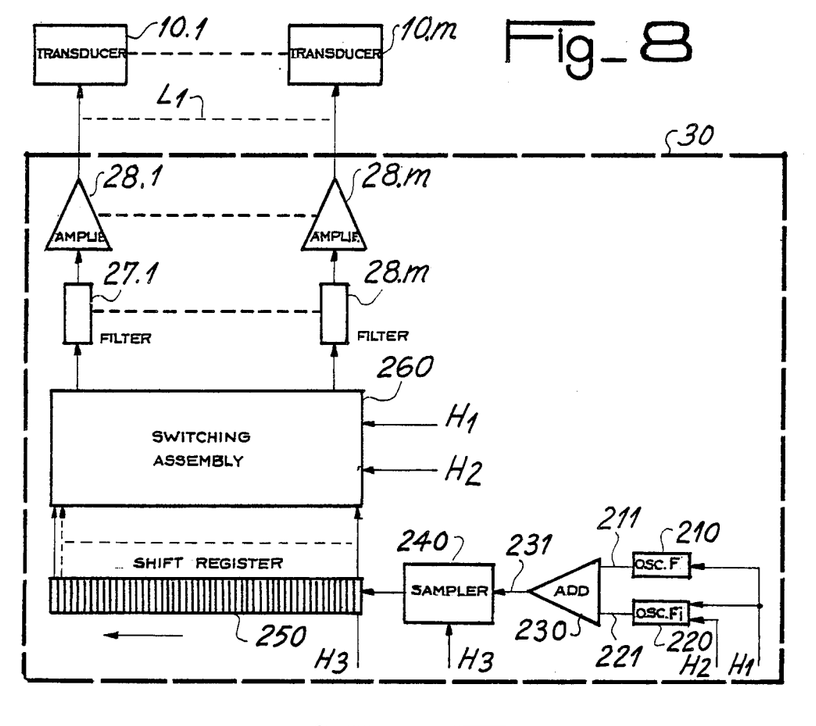
FIG. 8 shows a schematic view of the transmission.

FIG. 8 shows how the transmission spatial channels are formed in generator 30 which is connected, as has been seen, to transmission transducer assembly 21. Clock signal $H_1$ (FIG. (FIG. 9a), which is delivered by circuits 80, opens up an oscillator 210 at frequency. The clock signals $H_1$ and $H_2$ (FIG. 9b) trigger an oscillator 220 at a variable frequency, and supplying a series of frequencies $F_1$, . . . $F_q$ r times in succession, r being the number of low frequency spatial channels to be formed. For example, oscillator 220 transmits on ten frequencies three times in succession. The reason for this sequential transmission is that the high frequency transducer power capacity is limited and does not allow transmission on all the frequencies in every direction simultaneously at the acoustic power level required for a good parametric output.

Figure 9:
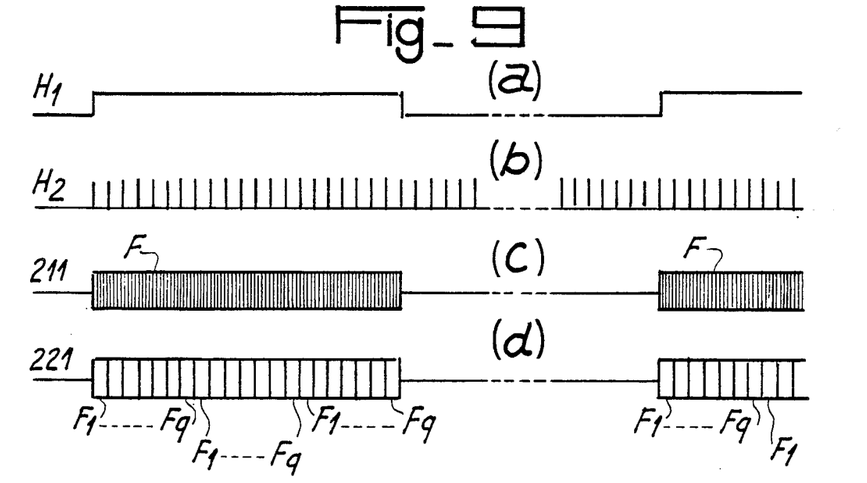
FIGS. 9a to 9d show various time signals.

The signals coming from oscillators 210 and 220 at 211 and 221 are shown in FIGS. 9c and 9d. They are mixed linearly in the summator 230, sampled at the rate $H_3$ in the circuit 240 and passed to a shift register 250 the number of elements being a function of the directional precision of the channels formed and of the maximum delay to be produced, i.e. of the direction of the channel the most off-aim.

Output connectors for the delayed data are judiciously arranged to feed the m transmission transducers through the link $L_{10}$ with N different successive delays through the analog switching assembly 260. The switching rhythm is that of clock $H_2$.

The signals are filtered in the filter circuits 27.1, . . . 27.m in the whole frequency band $F_1$, . . . $F_q$ and F. The filtered signals are amplified by the power amplifiers 28.1, . . . 28.m and fed to transducers 10.1, . . . 10.m by link $L_1$.

Figure 10:
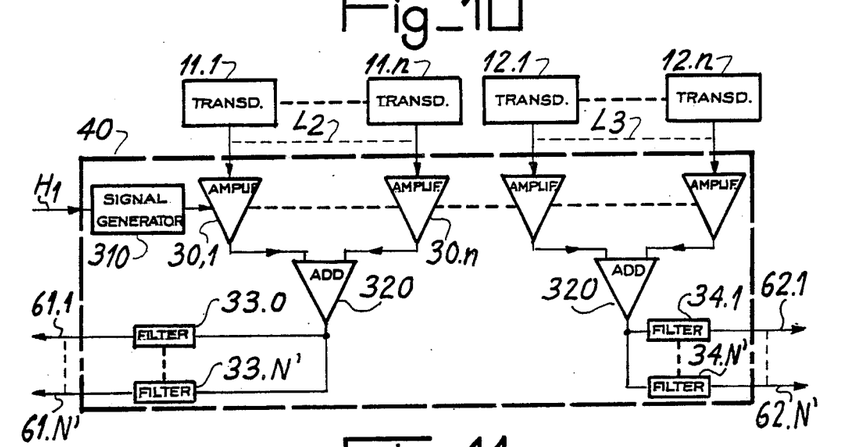
FIG. 10 shows the schematic diagram of the formation of the high frequency channels on transmission.

FIG. 10 shows the detail of reception assembly 40 which includes the two channels of the frequential high frequency channels $F_1$, . . . $F_N$, which are formed in the high frequency spatial centre channel as was previously indicated in connection with FIG. 6.

These two channels are identical. For the first channel, the signals coming from the reception high frequency transducers 11.1, . . . 11.n are amplified by amplifiers 30.1, . . . 30.n, whose gain is adjusted cyclically by the signal generator 310, to weight the echoes as a function of their range, the generator itself being controlled by clock signal $H_1$ delivered by assembly 80. These signals are summed by the n-input summator 320.

They are filtered by the narrow band band-pass filters 33.1, . . . 33.N' which are tuned respectively to the series of primary frequencies $F_1, \ldots F_N$, to within the Doppler frequency which are 10 in number for example corresponding to the ten directions of the centre space.

As has been said, for the second channel, the same circuits as above are found after the reception high frequency transducers 12.1 to 12.n, i.e. the amplifiers 300.1 to 300.n, a summator 320 and the narrow band band-pass filters 340.1 to 340.N'.

Figure 11:
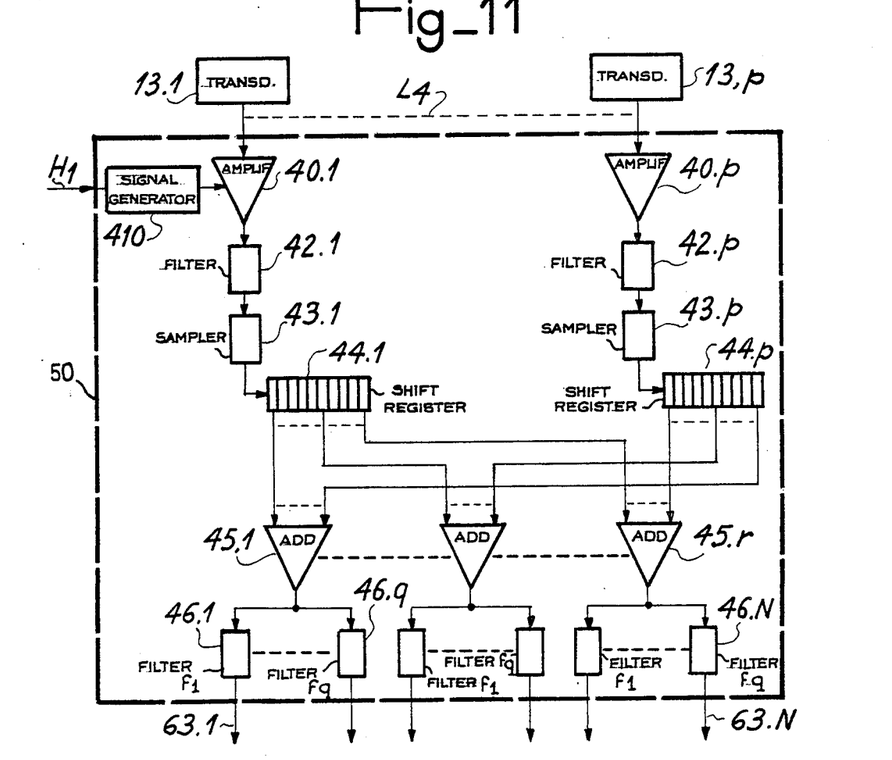
FIG. 11 shows the schematic diagram of the formation of the low frequency channels on reception.

FIG. 11 shows the block diagram of low frequency channel formation in reception assembly 50. The signals received from transducers 13.1, . . . 13.p are amplified by the amplifiers 40.1, . . . 40.p whose gain is adjusted cyclically by the signal generator 410, which is itself controlled by clock signal $H_1$ coming from assembly 80. The signals are filtered in the secondary frequency band $f_1 = F - F_1$ to $f_q = F - F_q$ by the band-pass filters 42.1, . . . 42.p. They are then sampled at the rate $H_4$ coming from assembly 80 in the circuits 43.1, . . . 43.p and the samples passed to shift registers 44.1, . . . 44.p. Judiciously arranged connectors, r in number on each register, enable the p samples to be summed in each of the r summators 45.1, . . . 45.R. The output of each summator is passed to q narrow band band-pass filters 46.1, . . . 46.q centred respectively on the frequencies $f_1, \ldots f_q$ within the Doppler frequency. Hence, at the output of the filters there are $r \times q$ low frequency channels formed in $r \times q$ directions.

Figure 12:
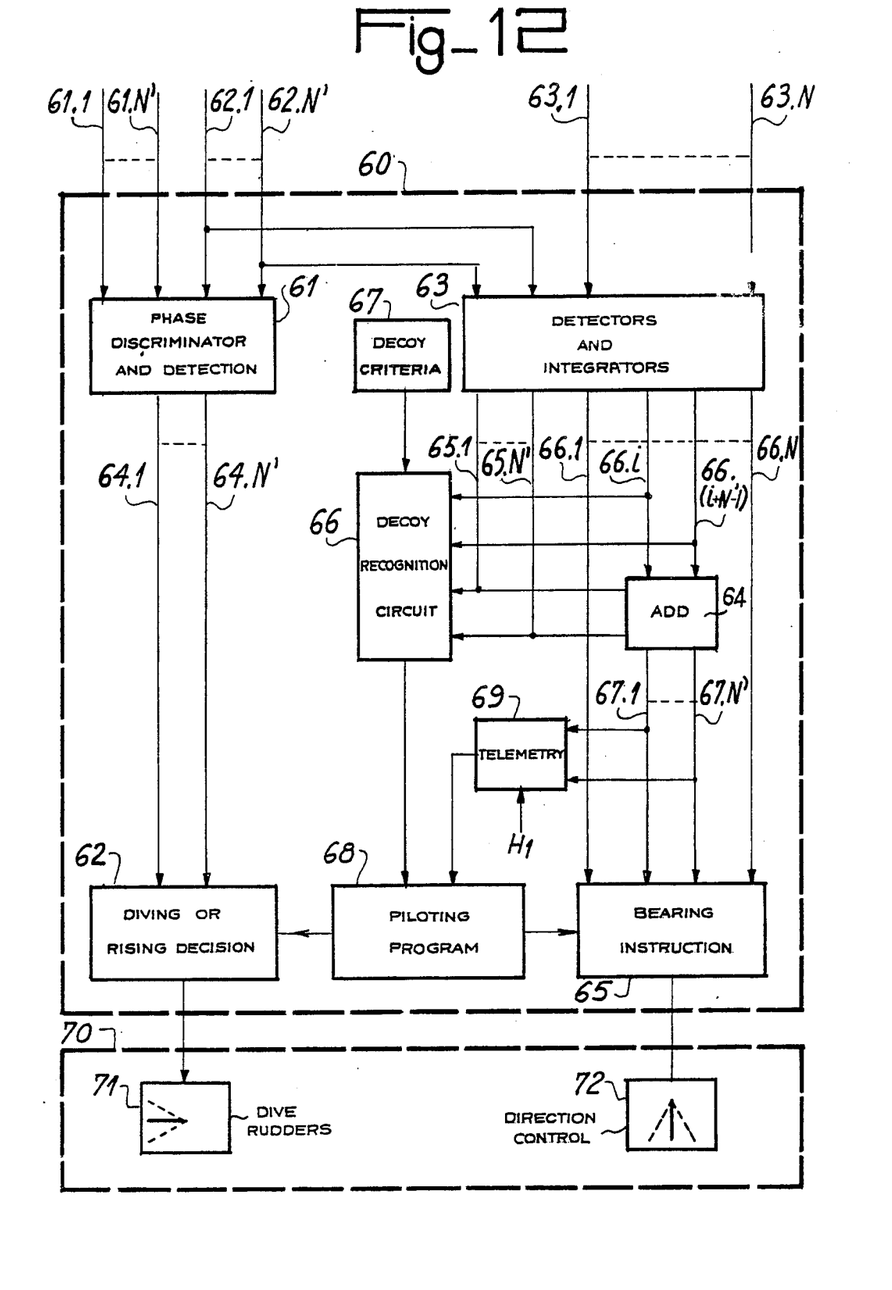
FIG. 12 shows the schematic diagram of the circuits comparing the high and low frequency reception signals used to control the torpedo rudders.

FIG. 12 shows the block diagram of decision circuit 60 and submarine vehicle rudder control circuit 70.

The high frequency transducer contains two rows of transducers separated vertically by $\lambda/2$ and so the signals corresponding to the same channel in bearing are out of phase. The phase shift sign depends on the sign of the angle of the normal to the transducer with the target direction, which corresponds to a target "above" or "below".

The two groups of signals 61.1, . . . 61.N' and 62.1, . . . 62.N' of the high frequency channels coming from reception assembly 40 (FIG. 10) are passed two by two to N' phase discriminator-integrators 61 and separated into N' detected signals 64.1, . . . 64.N' containing the target high-low data.

Circuit 62 prepares an instruction for the which to dive or rise in the presence of echoes in one or several of the N' high frequency channels. The decisions of circuit 62 are passed to the dive rudders 71.

Circuit 63 receives the signals 63.1, . . . 63.N' from low frequency channels together with those from one of the high frequency channels 62.1, . . . 62.N'. These signals are detected and integrated in succession over several recurrence cycles.

Among the N signals, 66.1, . . . 66.N, detected and integrated at low frequency, some 66.i, . . . 66.(N'+i−1) come from exactly the same directions in bearing as the detected and integrated signals 65.1, . . . 65.N'. However, as was seen above an in accordance with one aspect of the invention, the detection of possible targets is improved by mixing the low frequency signals with the high frequency ones with a different variance which come from the same direction.

In circuit 64 the signals corresponding to the same direction at high frequency and low frequency are added. They are 65.1 to 66.1, . . . 65.N' to 66. (N'+i−1).

The purpose of circuit 64 is to obtain the mean by an addition followed by amplitude regulation for each of the N' high and low frequency channels 65.1 and 66.1, . . . 65.N' and 66. (N'+i−1).

Hence, for the preparation of direction instructions, N low frequency signals covering the whole angular sector in bearing and N' signals which are the mean of the signals in the high and low frequency channels are available. These signals are received by circuit 65 which produces the bearing instructions and passes them to the direction controls 72.

At long range where the search phase occurs, only the low frequency channels 66.1, . . . 66.N detect the target echoes. Circuit 65, to which the low frequency channels are connected, compares the levels of the various echoes received. The target echo is the one whose level is usually the highest; the knowledge of the spatial and frequential channel in which it is enables the rudder instruction in bearing to be produced.

Under these conditions, the vehicle moves in direction to align its axis with the direction of the target. The low frequency signals are then more and more in the channels near the axis.

At the relatively short range where the so-called attack phase occurs, the vehicle is sufficiently close to the target for the target echoes to appear in the high frequency channels. As the variance decreases, a better comparison of the echo levels can be obtained.

Circuit 66 enables a decoy to be recognized. To do this it compares the number and amplitude of the echoes present, in accordance with the criteria preprogrammed in circuit 67, in the N' centre channels both at high and low frequency.

The decoys generally used reply in a limited frequency band usually used for distant vehicle guidance. They do not reply to both the high and low frequencies chosen in the production described.

The main characteristic of a decoy is to be seen as almost a point target until within the last few meters.

One type of anti-decoy programming of circuit 67 consists, for example, in determining with circuit 66 the number of echoes present in the high and low frequency channels and in deciding that a decoy is present if, during the attack phase, there is an echo in only one channel for several recurrences.

The antidecoy instruction is transmitted to the submarine vehicle piloting programmer 68 so that the vehicle changes its trajectory and returns to searching. Circuit 69, using clock signal $H_1$ and the delay in the echoes received in channels 67.1, . . . 67.N', produces a telemetry signal, which is used to inhibit the anti-decoy signal during the search phase where a large size target also appears as a point target.

Another advantage obtained with the invention is that the low frequency interference echoes coming from reflection from the free surface are very weak when the torpedo is moving near it.

The secondary frequency beam amplitude produced before reflection at the surface changes sign after reflection. The amplitudes of the two primary beams which are reflected at the surface also change sign after reflection. These two beams give rise to a second secondary beam whose amplitude is opposite in phase to that of the first secondary beam reflected. This gives a big attenuation of the resulting low frequency echo.

The use of non-linear acoustics in the guidance in bearing of a submarine vehicle to a distant target enables the whole aperture of the diagram in elevation to be retained. This is necessary to ensure vertical angular cover.

A system of self-guidance for submarine vehicles has been described with a greater range for target acquisition and a greater angular precision for guidance than devices of preceding art.

What I claim is:

1. A self guidance system for a submarine vehicle moving toward a target near the surface of the sea and carrying a parametric sonar comprising:

means for transmitting sound waves means for receiving sound waves reflected from a target means for forming r receiving beams wherein $r \geq 2$ in an angular aperture of bearing so as to define r sectors in said aperture, means for forming $r \times q$ transmitting beams, wherein $q \geq 2$ so as to define q subsectors in said r sectors first generator means generating a main frequency F and second generator means generating q frequencies $F_1, F_2 \ldots F_i \ldots F_q$ said latter being called primary frequencies or high frequencies switching means connected to said second generator means for selecting one of said primary frequencies $F_1, F_2 \ldots F_i \ldots F_q$, a plurality of filtering means, each centered on one of secondary frequencies, such as $f_1 = F - F_1$, $f_2 = F - F_2 \ldots f_i = F - F_q$, first clock generator means $H_1$ of period $T_1$, $T_1$ being the period of transmitting said main frequency second clock generator means of period $T_2$, $T_2$ being the duration of transmitting at one of said primary frequencies, both said clock generator means controlling said first and second generator means an adding circuit connected to said first and second generator means delivering to said transmitting beams forming means signals on said main frequency and on one of said selected primary frequencies, said transmitting beams forming means being controlled by said clock signals $H_2$, forming a beam in one of said $r \times q$ subsectors said receiving means receiving sound waves reflected from a target on said secondary frequencies, being connected to said receiving beam forming means, latter being controlled by said clock signals $H_2$ and $H_1$, forming beams in one of said r sectors, said plurality of filtering means centered on each secondary frequency receiving the signals from said receiving beam forming means and at the output of said filtering means are obtained the q receiving channels called frequential channel for each of said sectors.

2. A self guidance system as claimed in claim 1 wherein said transmitting means comprises an assembly of transducers called transmitting antenna.

3. A self guidance system as claimed in claim 1 wherein said receiving means comprises an assembly of transducers called secondary frequency receiving antenna.

4. A self guidance system as claimed in claim 1 wherein said receiving means comprises further another assembly of transducers called primary frequency receiving antenne, said letter antenna being connected to a plurality of N' filters centered at N' primary frequencies where $N' \leq q$. forming N' channels called primary frequential channels.

5. A self guidance system as claimed in claim 4 wherein said primary reception antenna comprises two rows of transducers, placed one above the other at a distance of $\lambda/2$, where $\lambda$ is the wave length in the sea propagation medium and said primary frequential channels are formed for each of the two rows.

6. A self guidance system as claimed in claim 4 comprising control means for controlling the elevation rudder of said submarine vehicle and comprising further comparison means, said comparison means receiving the signals of the same echo in two frequential channels corresponding to the two rows of said primary frequency receiving antenna, the output of said comparison circuit being applied to said control circuit for the elevation rudder.

7. A self guidance system as claimed in claim 5 comprising control means for controlling the bearing rudder of said submarine vehicle and comprising adding circuit means for adding the received signals in two corresponding primary and secondary frequential channels the output of said adding circuit being applied to said control means for the bearing rudder.

8. A self guidance system as claimed in claim 7 comprising further decoy recognition circuit means receiving the signals of two corresponding primary and secondary frequential channels, the output of said decoy recognition circuit being connected to piloting program means controlling the said control means for the bearing and the elevation rudders.

9. A self guidance system as claimed in claim 1 wherin said first generator means supplying sinusoidal signals at frequency F is driven by said $H_1$ clock generator, said second generator means comprising frequency synthetizer driven by said clock generators $H_1$ and $H_2$ supplying sequentially at said rate $T_2$ said frequencies $F_1, F_2 \ldots F_i \ldots F_1$ the signals at frequencies F and $F_i$ being applied to said adding circuit means, the output being sampled by sampling means at the rate of a clock $H_3$ the signals entering a CCD (charge couple device) analog shift register with multiple connectors, the outputs of said multiple connectors being applied to adding circuits giving the signals for the different receiving beams.

10. A self guidance system as claimed in claim 8 wherein the signals received by each of the transducers of said two rows is applied to an amplifier the gain of which is under the control of a program circuit connected to said clock generator $H_1$.

11. A self guidance system as claimed in claim 5 wherein said secondary frequency reception signals are applied to amplifiers the gain of which is adjusted under the control of said clock $H_1$ each of the amplified signals being applied to a sampler and connected to multiple connectors analog shift register the signals from said multiple connectors being applied to adding circuit means connected to the said filtering means at said secondary frequencies $f_1, f_2 \ldots f_i, f_n$.

* * * * *